United States Patent [19]

Kleshinski

[11] Patent Number: 5,485,667

[45] Date of Patent: Jan. 23, 1996

[54] METHOD FOR ATTACHING A MARKER TO A MEDICAL INSTRUMENT

[76] Inventor: Stephen J. Kleshinski, 599 Country Way, Scituate, Mass. 02066

[21] Appl. No.: 205,106

[22] Filed: Mar. 3, 1994

[51] Int. Cl.[6] .................................................. B23P 11/02
[52] U.S. Cl. .......................... 29/447; 29/469.5; 29/517; 29/523
[58] Field of Search .................................. 29/447, 469.5, 29/507, 508, 517, 523; 285/381; 403/273; 604/281

[56] References Cited

U.S. PATENT DOCUMENTS

| | | |
|---|---|---|
| 4,198,081 | 4/1980 | Harrison et al. . |
| 4,227,293 | 10/1980 | Taylor ........................................ 29/447 |
| 4,771,776 | 9/1988 | Powell et al. ........................... 604/281 |
| 4,807,626 | 2/1989 | McGirr ..................................... 604/281 |
| 4,964,853 | 10/1990 | Sugiyama et al. ......................... 604/96 |
| 5,019,040 | 5/1991 | Itaoka et al. . |
| 5,019,057 | 5/1991 | Truckai . |
| 5,078,684 | 1/1992 | Yasuda . |
| 5,125,143 | 6/1992 | Takahashi ............................... 29/469.5 |
| 5,213,111 | 5/1993 | Cook et al. . |

*Primary Examiner*—David P. Bryant
*Attorney, Agent, or Firm*—Sixbey, Friedman, Leedom & Ferguson

[57] ABSTRACT

The method for securely attaching a radiopaque marker device to a medical instrument, such as a catheter, comprises the steps of providing a medical instrument, providing a marker device formed of a radiopaque shape-memory material, such as Nitinol, having a deformed configuration while at a first temperature, positioning the marker device adjacent the catheter, and changing the first temperature of the shape-memory material to a second temperature sufficient to cause the shape-memory material to transform from the deformed configuration to an original configuration so that the marker device engages the catheter upon return of the shape-memory material to the original configuration. The marker device may include a cylindrical band positioned concentrically around a tubular portion of the instrument so that heating of the shape-memory material is sufficient to allow the band to melt the tubular portion and move into embedded engagement with the tubular portion when in the original configuration. The step of changing the first temperature of the shape-memory material to the second temperature may result in the outer radial extent of the band extending no further radially outwardly than the outer surface of the tubular portion thereby maintaining the constant outer diameter of the tubular portion of the instrument. The resulting medical instrument includes a marker device specifically attached to the instrument by the thermally induced deformation of the shape-memory material from the deformed configuration to the original configuration.

21 Claims, 3 Drawing Sheets

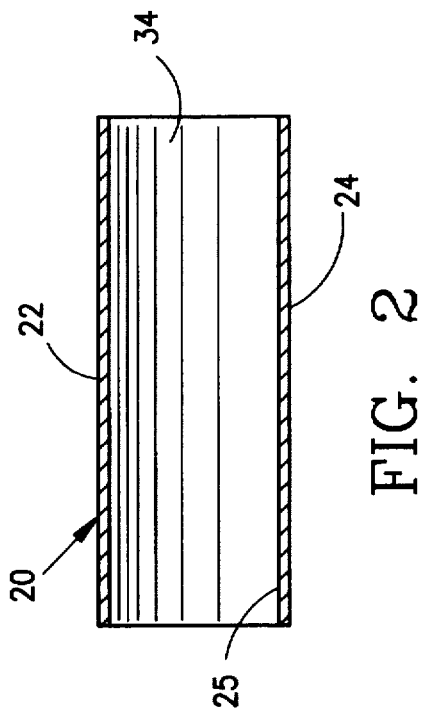
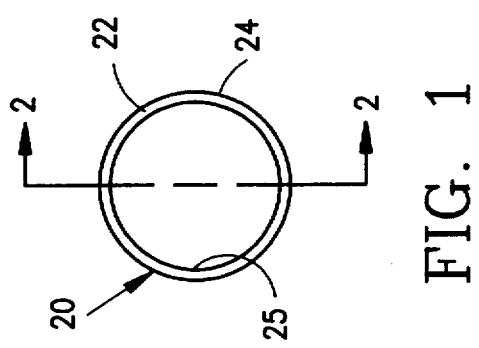
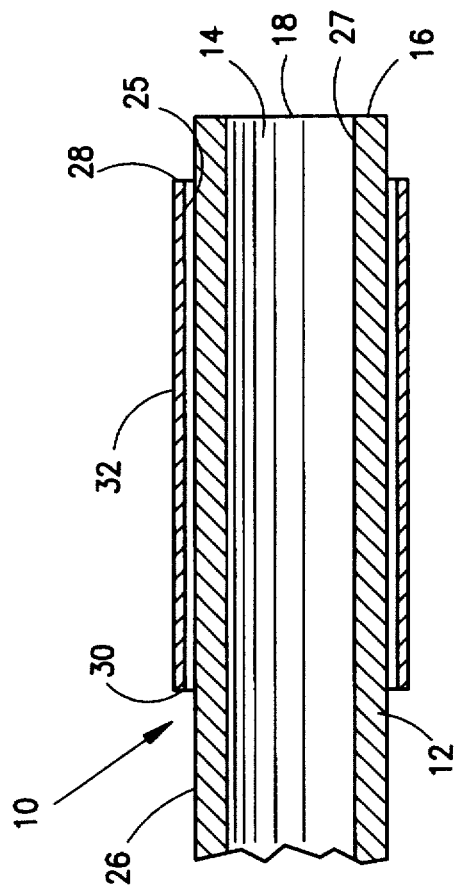
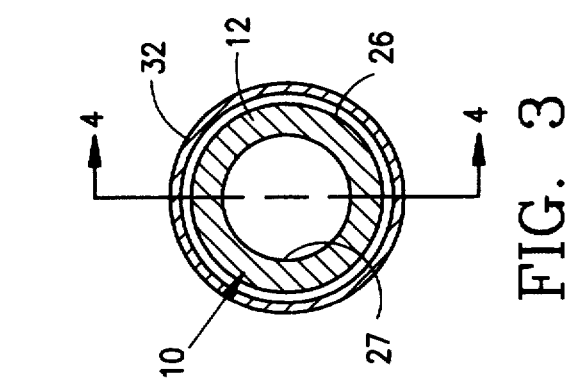

METHOD FOR ATTACHING A MARKER TO A MEDICAL INSTRUMENT

TECHNICAL FIELD

This invention relates to a medical instrument, such as a catheter, for treating a patient, and a method for making such an instrument, which aids the user in accurately determining the location of the medical instrument relative to the patient.

BACKGROUND OF THE INVENTION

In the medical industry there is widespread use of medical instruments, such as catheters and angioplasty balloons, which are inserted into the patient's body to permit surgical repair, maintenance and examination. For example, catheters generally include a hollow tubular portion, usually formed of resilient plastic, for insertion through the skin of a patient into a cavity, duct or vessel to permit injection or withdrawal of fluids, or to deliver medications to patients for therapeutic reasons. Regardless of the instrument, the accurate placement of the instrument in the patient's body is often critical to its successful use. Moreover, catheters are increasingly being used to introduce a mechanical device into the body through the catheter which, when exiting the catheter, unfolds or springs open into an operating position. Examples of such devices include vena cava filters used to trap blood clots, and stents used to hold blood vessels open. These applications are substantially different than the simple administration of fluids in that the proper function of the mechanical device being passed through the catheter is often even more dependent upon its accurate placement in the patient's body.

As a result, attempts have been made to assist the physician in viewing the catheter during use to assist in the accurate positioning of the device. For example, X-ray reflective chemicals may be used in forming the plastic tubular portion of the catheter to allow the physician to view the catheter using X-ray radiography. Often, however, these specially made catheters remain very difficult to see. For catheters being used to position a mechanical device such as a stent, other methods have been used to improve the visibility of the catheter. For example, to accurately place a stent at a predetermined location in a blood vessel, the physician will first place the tip of the catheter, used to deliver the stent, at that location. The physician knows the catheter tip is correctly placed by injecting a small amount of X-ray reflective solution or "dye" through the catheter, and observing where the dye emerges in the blood vessel. However, as soon as the dye dissipates in the blood flow, the location of the tip of the catheter is no longer as obvious. Regardless, the physician continues with the procedure by pushing the stent (which is plainly visible on X-ray) through the catheter. The physician must watch the stent closely during this time for any sign that it is beginning to open since this is the only way to determine whether the stent has reached the open distal tip of the catheter. However, the physician has no way of knowing if the catheter itself (which still contains the stent) has moved. Therefore, even though the physician knows the stent is about to exit the catheter, it is uncertain whether the stent will be placed exactly in the position desired.

In an attempt to solve the above-noted deficiencies, some catheter manufacturers position a marker device in the form of a radiopaque material near the distal end of the medical instrument. For example, U.S. Pat. No. 5,213,111 discloses a wire guide for a catheter including a coil spring formed of a radiopaque material, such as platinum, positioned around an inner strand which also may be platinum or gold. This design better enables the physician using the wire guide to determine its exact location via X-rays. However, this design is complex and requires a rather large amount of expensive radiopaque material thus increasing the cost of the device. Also, once the catheter has been guided into place and the wire guide removed, it is difficult to monitor the location of the catheter. Various other catheter manufacturers mark the catheter by gluing a marker device in the form of a band of radiopaque material, such as platinum or gold, to the tubular portion near the distal end of the catheter so that the physician can always see the exact location of the catheter. Although these bands are very thin, the outer radial extent of the band still extends beyond the outer radial surface of the catheter creating an annular ridge at each end of the band. These ridges can create difficulties when inserting the catheter into the blood vessel including causing an uncomfortable feeling to the patient. Also, since the band is glued on, it can only be applied to certain materials which permit secure bonding of the glue. Moreover, even then, the band may be detached from the catheter without much difficulty.

Catheters and other medical devices have also been formed of shape-memory alloys and resins, such as a nickel-titanium alloy often called Nitinol. These materials exhibit anthropomorphic qualities of memory and trainability such that when the alloy is heated above a certain transition temperature, a desired shape which has been processed into the material for that temperature is restored regardless of the shape or configuration prior to heating. These materials may be deformed considerably when at a lower temperature but will completely recover to their configuration on being heated above the specified transition temperature. For example, U.S. Pat. Nos. 5,019,040, 5,019,057 and 5,078,684 all disclose catheter devices formed partially of shape-memory alloys which allow the shape of the catheter to be advantageously modified during use. However, these references fail to disclose catheters having simple, yet effective, marker devices which can be easily, inexpensively and yet securely attached to the catheter for enabling the physician to accurately locate the position of the catheter during use relative to the patient.

U.S. Pat. No. 4,198,081 to Harrison et al. discloses a coupling formed of a shape-memory material which uses the shape-recovering properties of the shape-memory material to connect two pipes together. However, the coupling is not used in the medical field as a marker device for a medical instrument. Moreover, this coupling device does not use the shape-recovery properties of the coupling to embed the coupling into the pipes to avoid the formation of an annular ridge at each end of the coupling.

SUMMARY OF THE PRESENT INVENTION

It is one object of the present invention to provide an improved medical instrument which can be easily and effectively located during use in a patient's body.

Another object of the present invention is to provide an improved medical instrument having a marker device for enabling a physician to accurately locate the position of the medical instrument in a patient's body while minimizing discomfort to the patient during use.

Yet another object of the present invention is to provide a novel and improved medical instrument, such as a catheter, having an inexpensive yet effective marker device which is securely attached to the instrument.

A further object of the present invention is to provide a novel and improved medical instrument, such as a catheter, having a marker device embedded in the catheter by securely attaching the marker device to the catheter while providing a catheter with a smooth outer surface having a substantially constant outer diameter.

Yet another object of the present invention is to provide a novel and improved medical instrument having a marker device formed of a shape-memory material and securely attached to the catheter by the shape-forming characteristics of the material.

A still further object of the present invention is to provide a simple, effective, inexpensive and reliable method for securely attaching a radiopaque marker device to a medical instrument.

Yet another object of the present invention is to provide a simple, yet effective, method for attaching a marker device to a medical instrument which avoids the formation of ridges on the outer surface of the instrument.

A further object of the present invention is to provide a novel method for attaching a marker device to a catheter which maintains constant both the outer and inner diameters of a tubular portion of the catheter thereby avoiding the formation of ridges on the outer surface while maintaining the functionality of the passageway extending through the catheter.

Yet another object of the present invention is to provide an effective, yet inexpensive, method for attaching a marker device to a catheter using the shape-recovery characteristics of a shape-memory material forming the marker device.

These and further objects of the present invention are achieved by providing a method for attaching a marker device to a medical instrument, such as a catheter, for insertion into the body of a patient which comprises the steps of providing a medical instrument, providing a marker device formed of a shape-memory material having a deformed configuration while at a first temperature, positioning the marker device adjacent the catheter, and changing the first temperature of the shape-memory material to a second temperature sufficient to cause the shape-memory material to transform from the deformed configuration to an original configuration, wherein the marker device engages the catheter upon return of the shape-memory material to the original configuration. The method may include the steps of cooling the marker device to the first temperature and deforming the marker device into the deformed configuration from the original configuration while the shape-memory material is at the first temperature. The second temperature may be greater than the first temperature so that the method includes heating the shape-memory material to the second higher temperature. The medical instrument or catheter may include a tubular portion having an outer surface for engagement by the marker device and an inner surface formed opposite the outer surface while the method may include the step of positioning a support rod adjacent the inner surface for supporting the tubular portion. The marker device may include a cylindrical band of radiopaque, shape-forming material positioned concentrically around the tubular portion of the catheter so that heating of the shape-memory material to the second temperature causes the tubular portion to soften as the heated band contacts the tubular portion allowing the band to move into embedded engagement with the tubular portion when in the original configuration. The step of changing the first temperature of the shape-memory material to the second temperature results in the outer radial extent of the band extending no further radially outwardly than the outer surface of the tubular portion thereby maintaining the constant outer diameter of the tubular portion of the catheter. The tubular portion may be formed of a thermoplastic polymer while the shape-memory material may be a nickel titanium alloy often referred to as Nitinol.

The objects of the present invention are also achieved by providing a medical instrument such as a catheter for use in treating a patient comprising a tubular portion and a marker device attached to the tubular portion for allowing the tubular portion to be located relative to the patient. The marker device is formed of a radiopaque shape-memory material positioned in an original configuration and capable of thermally induced deformation from a deformed configuration to the original configuration. The marker device is specifically attached to the tubular portion by the thermally induced deformation of the shape-memory material from the deformed configuration to the original configuration. The marker device may include a cylindrical band having an outer radial extent which extends radially outwardly no further than the outer radial extent of the tubular portion.

BRIEF DESCRIPTION OF THE DRAWINGS

FIG. 1 is an end view of the marker device of the present invention;

FIG. 2 is a cross-sectional view of the marker device of the present invention taken along plane 2—2 in FIG. 1;

FIG. 3 is a cross-sectional view of the medical instrument and the marker device in the deformed configuration prior to attachment to the medical instrument;

FIG. 4 is a cross-sectional view of the medical instrument prior to attachment of the marker device taken along plane 4—4 in FIG. 3;

DETAILED DESCRIPTION OF THE PREFERRED EMBODIMENT

Figure 5:
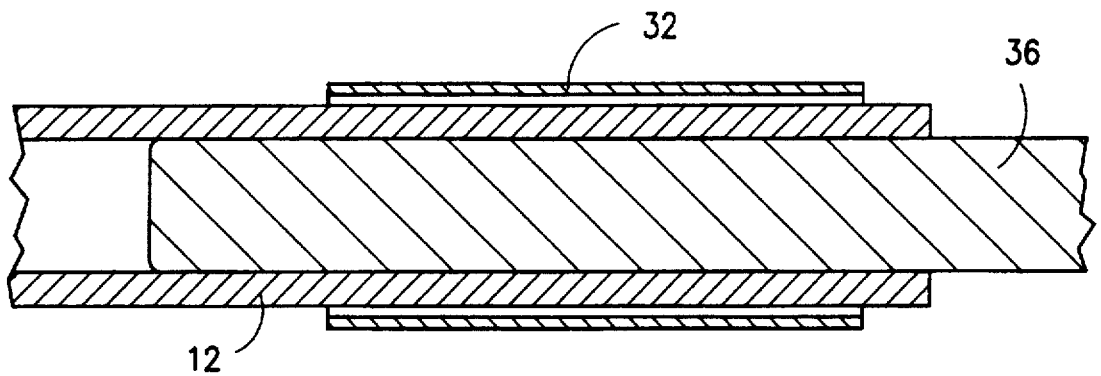
FIG. 5 is a longitudinal, cross-sectional view of the medical instrument prior to attachment of the marker device with a support rod positioned in the instrument.
Figure 6:
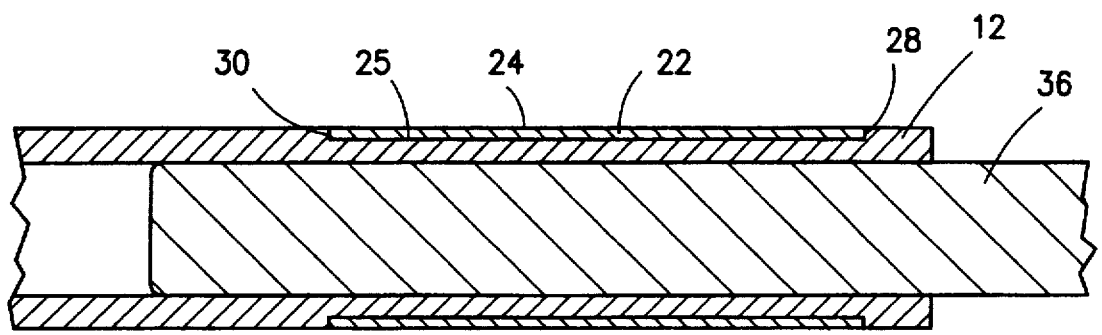
FIG. 6 is a longitudinal cross-sectional view of the medical instrument with the marker device in embedded engagement with the medical instrument corresponding to the original configuration of the marker device and prior to removal of the rod.
Figure 7:
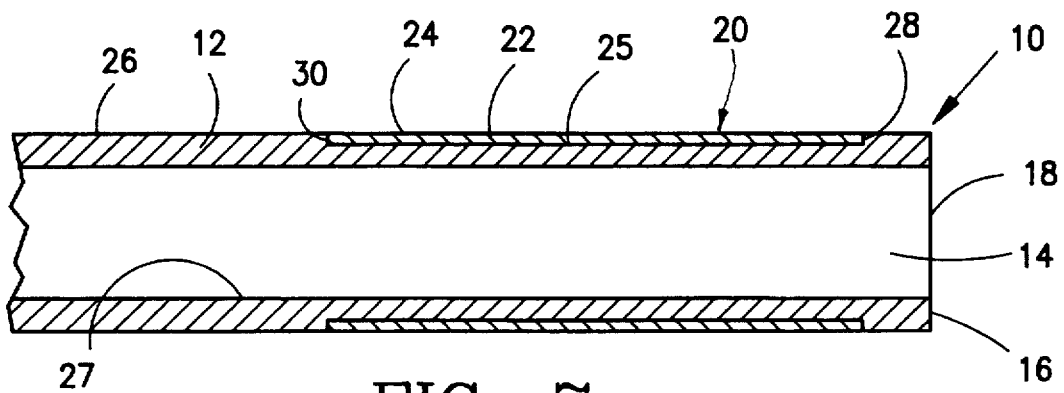
FIG. 7 is a longitudinal cross-sectional view of the medical instrument of the present invention with the support rod removed.
Figure 8:
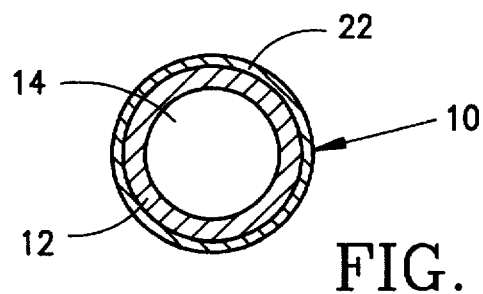
FIG. 8 is a transverse cross-sectional view of the medical instrument of the present invention with the marker device embedded in the instrument.

The novel medical instrument of the present invention indicated generally at 10 in FIGS. 7 and 8 is formed by the novel method of the present invention as illustrated in FIGS. 1–7. For convenience, the medical instrument of the present invention will be discussed hereinbelow followed by a description of the method of the present invention.

As shown in FIGS. 7 and 8, the medical instrument 10 includes an extension 12 for insertion into the body of a patient (not shown). In the preferred embodiment, the extension 12 may be a tubular portion of, for example, a catheter, having a passageway 14 for directing fluids or mechanical devices, such as stents, to and from the body of the patient. The extension or tubular portion 12 includes a distal end 16 which defines an opening 18 of passageway 14. Tubular portion 12 also includes an outer radial surface 26 and an inner radial surface 27 defining passageway 14. The tubular portion 12 of the instrument may be formed of any appropriate material which is desirably used for insertion into the human body but is preferably formed of a flexible material such as polyethylene, nylon, PVC, polyurethane or silicone rubber.

During use, it is often critical that the distal end 16 of the medical instrument 10 be accurately positioned adjacent the work area within the patient's body which is to be examined or treated. Consequently, medical instrument 10 of the present invention includes a marker 20 formed of a x-ray reflective, or radiopaque, material which may be viewed by the physician via radiography or fluoroscopy. Marker 20 is attached to instrument 10 adjacent distal end 16 so as to accurately mark the position of distal end 16 when exposed to x-rays. Preferably, marker 20 is a cylindrical band 22 having an outer radial extent 24 and an inner radial surface 25 defining a center bore 34 which terminates at one end 28 and at an opposite end 30. Cylindrical band 22 is embedded in outer radial surface 26 of tubular portion 12 using the novel method described herein below so that outer radial extent 24 extends no further radially outward than outer surface 26 of tubular portion 12. As a result, outer radial surface 26 of the tubular portion 12 is substantially continuous without interruptions or outwardly extending ridges formed by the ends 28, 30 of band 22.

Cylindrical band 22 is formed of a radiopaque material which exhibits anthropomorphic qualities of memory and trainability which is commonly referred to as a shape-memory material. For instance, cylindrical band 22 may be formed of the shape-memory alloy Nitinol which is a very radiopaque nickel titanium alloy. Shape-memory materials are manufactured to transform into, and maintain, an original configuration or shape when the temperature of the material is raised above a selected transition temperature. At certain temperatures lower than the transition temperature, the shape-memory alloy becomes somewhat ductile and can be deformed considerably into a desired deformed configuration. However, when the alloy is heated above the specific transition temperature, the desired original configuration which has been processed into the shape-memory material is restored regardless of the deformed configuration prior to raising the temperature above the transition temperature. Usually the transition temperature is higher than the temperature at which the shape-memory alloy may be deformed so that the alloy may be deformed into a deformed configuration at a relatively low temperature while the original configuration is recovered by heating the alloy to raise the temperature above a higher transition temperature.

Cylindrical band 22 of marker 20 is attached to tubular portion 12 by the thermally induced deformation or recovery of the shape-memory alloy from a deformed configuration as shown in FIGS. 3–5 to an original configuration as shown in FIGS. 6–8. As described more fully hereinbelow in relation to the method of the present invention, cylindrical band 22 is securely attached, and embedded into, tubular portion 12 by the thermally induces forces imparted by the band 22 when in the original configuration against outer radial surface 26 of tubular portion 12.

The method of the present invention for attaching marker 20 to tubular portion 12 of medical instrument 10 includes providing a cylindrical band 22 formed of a radiopaque shape-memory material having an outer diameter when in the original configuration of FIGS. 1 and 2 which is substantially equal to or less than the outer diameter of tubular portion 12 as defined by outer radial surface 26. The cylindrical band 22 is then cooled to a sufficiently low temperature below the shape recovering transition temperature so as to cause the shape forming material to become capable of physical deformation by an outside force. Cooling of the shape-memory material may be accomplished by any conventional cooling device capable of lowering the temperature of the shape-memory material into the desired low temperature range, such as a cooling device using liquid nitrogen. While the shape-memory material is at the low temperature, the cylindrical band 22 may be deformed into a deformed configuration illustrated by cylindrical band 32 in FIGS. 3 and 4 which has a larger diameter than band 22 of the original configuration shown in FIGS. 1 and 2. Larger diameter deformed cylindrical band 32 may be obtained by applying a radially outward force to the inner surface of band 22 by, for example, forcing a shaping rod through the center bore 34 of band 22. Of course, the shaping rod should have an outer diameter no less than the outer diameter of tubular portion 12 so that the deformed cylindrical band 32 may be slid over tubular portion 12. Once band 22 has been deformed from its original configuration into its deformed configuration as represented by deformed cylindrical band 32, deformed band 32 is positioned concentrically around tubular portion 12 adjacent distal end 16 as shown in FIG. 4. It should be understood that the illustrated deformation is exaggerated to include a rather large clearance gap between deformed band 32 and outer surface 26 of tubular portion 12 merely for purposes of clarity. In normal situations, the deformation will probably be considerably less than that illustrated. Typical deformation is, however, sufficient to allow tubular portion 12 to be slid through center bore 34 of band 32 while also permitting band 32 to move into sufficient embedded engagement with tubular portion 12 upon returning to the original configuration when the temperature of the shape-memory material is raised above the transition temperature as explained hereinbelow.

Prior to raising the temperature of the shape-memory material of band 32, a supporting mandrel or rod 36 is inserted through passageway 14 of tubular portion 12 so as to extend longitudinally along band 32 beyond both ends 28 and 30 as shown in FIG. 5. The temperature of the shape-memory material of band 32 is then raised above the predetermined transition temperature of the shape-memory material by heating band 32 using, for example, hot air or induction-type heating. As the shape-memory material of band 32 is raised to a temperature above the transition temperature, the band 32 begins to return to its smaller diameter original configuration by moving radially inward into contact with outer radial surface 26 of tubular portion 12. Continued movement by band 32 radially inwardly causes inner surface 25 of band 32 to press against outer radial surface 26 of tubular portion 12. Simultaneously, the temperature of band 32 is high enough to soften and even melt the thermoplastic polymer material of tubular portion 12 immediately adjacent band 32. As a result, band 32 sinks into the thermoplastic polymer of tubular portion 12 until it reaches its original configuration as represented by cylindrical band 22 in FIGS. 6–8. During the thermally induced deformation or shape recovery process into the original configuration, the support rod 36 supports the inner radial surface 27 of tubular portion 12 against the radially inward force of band 32 thereby maintaining the inside diameter of the tube. The support rod 36 is then removed resulting in a radiopaque marker securely embedded in a medical instrument.

In use, the tubular portion 12 of medical instrument 10 is inserted into a patient's body to perform one or more of a variety of functions including the delivery and withdrawal of fluids and mechanical devices such as stents. As is apparent, the present invention may be used to attach radiopaque markers formed of radiopaque shape-memory materials to many different types of medical instruments including angioplasty balloons and other endoscopic, laproscopic and arthroscopic instrumentation. Also, the method of the present invention can be used to attach angioplasty balloons, and other devices, to a catheter or other instrument by positioning the balloon between the band and the catheter before raising the temperature of the band. Once the temperature is raised and the band engages the catheter, the balloon will be securely attached to the catheter. When the instrument is positioned in the patient's body and the body exposed to x-rays, the radiopaque marker provides a clear indication to the physician as to the precise location of the marked portion of the instrument. The marker may also be provided with indicia marked or etched into the outer surface of the band. This indicia may be visible when exposed to x-rays during use so as to assist the physician in the procedure by, for example, distinguishing the catheter from an adjacent catheter.

The present invention has many advantages which include providing a simple and inexpensive method for securely attaching a radiopaque marker to a medical instrument. Since the cylindrical band melts its way into embedded engagement with the medical instrument when moving into a physically rigid configuration, no adhesives or other less dependable securing means must be relied on to hold the band in place. The band is simply more securely attached to the catheter than other conventional methods thereby minimizing risk of inadvertent detachment from the instrument.

Secondly, by sizing the band so that the outer diameter of the original configuration is no greater than the outer diameter of tubular portion 12 of the instrument 10, marker 20 can be effectively attached to instrument 10 without creating any dimensional changes or transitions such as ridges on outer radial surface 26 of tubular portion 12 thereby maintaining a smooth outer radial surface on the instrument 10. A smooth outer surface is advantageous on most medical instruments that are to be inserted into a patient's body since the outer surface must slide against the patient's skin and internal tissue. A smooth outer surface allows the medical instrument to more easily be pushed through a patient's skin or other openings having small clearances while minimizing damage to the patient. This advantage is particularly beneficial in the use of a catheter in certain operations wherein the catheter must be slid over a wire guide into a blood vessel or a wound through little or no clearance between the outer diameter of the wire guide and the internal tissue. The catheter can be more easily pushed through the clearance with less discomfort to the patient by providing a smooth surface free of dimensional transitions or ridges.

In addition, the present invention maintains the inside diameter of the medical instrument or catheter 10 constant. A constant inner diameter is especially important in catheters wherein mechanical devices are being pushed through passageway 14 of the catheter. Areas of smaller diameter or restrictions in passageway 14 could hinder or prevent the movement of the mechanical device. The present invention prevents the formation of internal restrictions in passageway 14 thereby maintaining a constant inner diameter by using support rod 36 and by utilizing the heat created in band 32 to melt band 32 into tubular portion 12.

Figure 9:
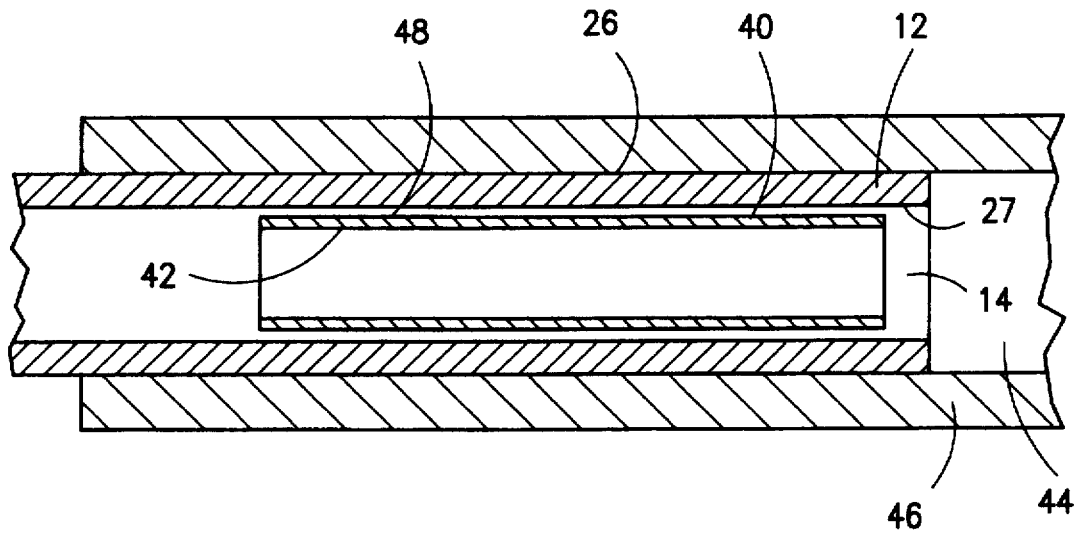
FIG. 9 is a longitudinal cross-sectional view of a second embodiment of the medical instrument of the present invention prior to attachment of the marker device with a supporting tube positioned around the instrument.
Figure 10:
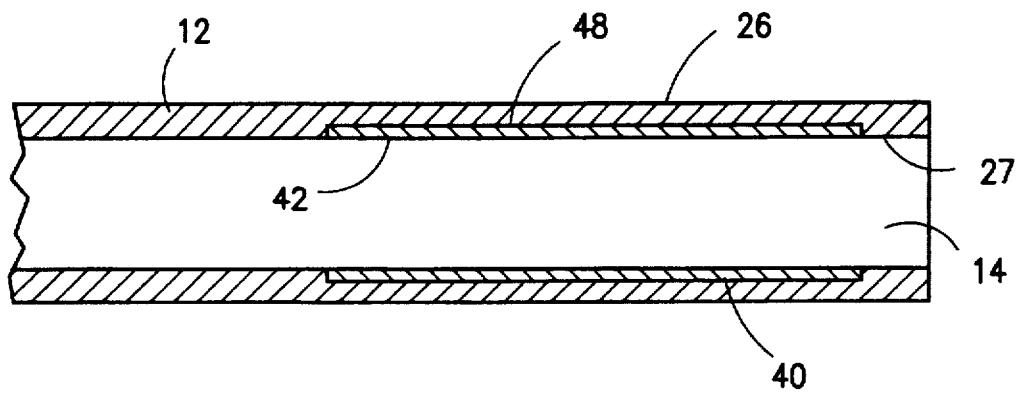
FIG. 10 is a longitudinal cross-sectional view of the second embodiment of the medical instrument of the present invention with the marker device attached and the supporting tube removed.

Referring to FIGS. 9 and 10, a second embodiment of the present invention is shown which is the same as the first embodiment except that a cylindrical band 40 is embedded into the inner radial surface 27 of tubular portion 12. Band 40 is made of a radiopaque, shape-memory material capable of changing shape from a deformed configuration shown in FIG. 9 to an original configuration shown in FIG. 10. The band 40 is sized, or chosen, so that its inner radial surface 42 has an inner diameter when in its original configuration which is no smaller than, and preferably approximately equal to, the inner diameter of passageway 14 formed by inner radial surface 27 of tubular portion 12. After being sufficiently cooled, band 40 is deformed into the configuration shown in FIG. 9 and positioned in passageway 14. Tubular portion 12 is then slid into a bore 44 of a supporting tube 46 having an inner diameter approximately equal to the outer diameter of tubular portion 12. The temperature of the shape-memory material of band 40 is then raised above the predetermined transition temperature of the shape-memory material by heating band 40 causing band 40 to begin to return to its larger diameter original configuration by moving radially outward into contact with inner radial surface 27 of tubular portion 12. Continued movement by band 40 radially outwardly causes outer surface 48 of band 40 to press against inner radial surface 27 of tubular portion 12. Simultaneously, the temperature of band 40 is high enough to soften and even melt the thermoplastic polymer material of tubular portion 12 immediately adjacent band 40. As a result, band 40 sinks into the thermoplastic polymer of tubular portion 12 until it reaches its original configuration as in FIG. 10. During the thermally induced deformation or shape recovery process into the original configuration, the supporting tube 46 supports the outer radial surface 26 of tubular portion 12 against the radially outward force of band 40 thereby maintaining the outside diameter of the tube. Supporting tube 46 is then removed resulting in a radiopaque marker securely embedded in a medical instrument.

INDUSTRIAL APPLICABILITY

The present method for attaching a radiopaque marker to a medical instrument heretofore described may be used attach radiopaque markers formed of a radiopaque shape-memory material to many different types of medical instruments including catheters, angioplasty balloons and various other endoscopic, laproscopic and arthroscopic instrumentation. Likewise, the resulting medical instrument having a radiopaque marker may be used in any medical or surgical procedure which requires x-ray visualization via radiography or fluoroscopy.

I claim:

1. A method for attaching a marker to a medical instrument used for treating a patient, comprising the steps of:

providing a medical instrument which includes a tubular portion having an outer surface engagement by said marker and an inner surface formed opposite to said outer surface;

providing a marker formed of a shape-memory material capable of having a deformed configuration while at a first temperature and an original configuration at a second higher temperature;

cooling said marker to said first temperature;

deforming said marker into said deformed configuration from said original configuration while said shape-memory material is at said first temperature;

positioning said deformed marker adjacent to the tubular portion of said medical instrument for subsequent engagement therewith;

positioning a support means adjacent to said inner surface for supporting said tubular portion prior to engaging said marker with said tubular portion; and changing said first temperature of said shape-memory material to said second temperature to cause said shape-memory material to transform from said deformed configuration to said original configuration, wherein said marker engages said medical instrument upon return of said shape memory material to said original configuration.

2. The method as defined in claim 1, wherein said second temperature of said shape-memory material is greater than said first temperature so that said step of changing said first temperature of said shape-memory material includes heating said shape-memory material to said second temperature.

3. The method as defined in claim 2, wherein said marker includes a cylindrical band, said step of positioning said marker including positioning said cylindrical band concentrically around said tubular portion of said medical instrument, said second temperature of said shape-memory material being sufficient to cause said cylindrical band to melt said tubular portion upon engagement with said tubular portion to allow said cylindrical band to move into embedded engagement with said tubular portion when in said original configuration.

4. The method as defined in claim 3, wherein said cylindrical band includes an outer radial extent, said step of changing said first temperature of said shape-memory material to said second temperature resulting in said outer radial extent extending no further radially outwardly than said outer surface of said tubular portion.

5. The method as defined in claim 4, wherein said medical instrument is formed of a thermoplastic polymer and said step of changing said first temperature to said second temperature includes heating said shape-memory material and said medical instrument using hot air.

6. The method as defined in claim 1, wherein said shape-memory material is also a radiopaque material.

7. The method as defined in claim 6, wherein said shape-memory material is a nickel titanium alloy.

8. A method for attaching a marker to a medical instrument used for treating a patient comprising the steps of:

providing a medical instrument wherein said medical instrument includes a tubular portion having an inner surface for engagement by said marker and an outer surface formed opposite to said inner surface, providing a marker formed of a shape-memory material capable of having a deformed configuration while at a first temperature and an original configuration at a second temperature;

positioning said marker in the deformed configuration adjacent to the inner surface of the tubular portion of said medical instrument for subsequent engagement therewith;

positioning a support means adjacent said outer surface for supporting said tubular-portion prior to engaging said marker with said tubular portion; and changing said first temperature of said shape-memory material to said second temperature to cause said shape-memory material to transform from said deformed configuration to said original configuration wherein said marker engages the inner surface of said tubular portion upon the return of said shape memory material to said original configuration.

9. The method as defined in claim 8, wherein said marker includes an inner surface when in said original configuration which extends radially inward no further than said inner surface of said tubular portion.

10. A method for attaching a marker to a medical instrument comprising the steps of:

providing a medical instrument having an outer surface and an inner chamber defined by an inner surface, providing a marker formed of a shape-memory material capable of having a deformed configuration while at a first temperature and an original configuration at a second temperature;

positioning said marker at said first temperature in the deformed configuration adjacent to one of said outer or inner surfaces of said medical instrument for subsequent engagement therewith;

positioning a support means for contact with the remaining inner or outer surface not to be subsequently engaged by said marker prior to engaging said marker so as to support said surface in the area of said medical instrument to be engaged by said marker; and changing said first temperature of said shape-memory material to said second temperature to cause said shape memory material to transform from said deformed configuration to said original configuration wherein said marker engages said medical instrument.

11. The method of claim 10 which includes providing a marker having an original configuration which is dimensioned so that said marker will deform the inner or outer surface of the medical instrument engaged thereby when the shape-memory material is transformed from said deformed configuration to said original configuration to engage said medical instrument.

12. The method of claim 11 wherein the inner or outer surface of said medical instrument to be engaged by said marker is formed of a thermally responsive material which is softened at a softening temperature, and wherein the temperature of said shape-memory material is raised to said softening temperature while changing from said first temperature to said second temperature to soften said thermally responsive material.

13. The method of claim 12 wherein said medical instrument is a catheter including a tubular portion of thermoplastic material having an outer radial surface of a first diameter and an inner radial surface of a second diameter defining said inner chamber and said method further including the steps of:

cooling said marker to said first temperature and deforming said marker to said deformed configuration prior to positioning said marker adjacent to one of said inner or outer radial surfaces.

14. The method of claim 13 wherein said marker is a cylindrical band having an inner diameter in the original configuration which is less than the first diameter of the outer radial surface, and wherein the step of deforming said marker to said deformed configuration includes increasing the inner diameter of the cylindrical band to a diameter sufficient to permit the cylindrical band to fit over the outer radial surface of said tubular portion, the step of positioning said marker includes positioning said cylindrical band concentrically around the outer radial surface of said tubular portion, and the step of positioning said support means includes inserting a support into said inner chamber to support the inner radial surface.

15. The method of claim 13 wherein said marker is a cylindrical band having an outer diameter in the original configuration which is greater than the second diameter of the inner radial surface, and wherein the step of deforming said marker to the deformed configuration includes reducing the outer diameter of the cylindrical band to a diameter sufficient to permit the cylindrical band to be inserted within the inner chamber, the step of positioning said marker includes positioning said cylindrical band within the inner chamber adjacent to the inner radial surface thereof, and the step of positioning said support means includes positioning a support concentrically around the outer radial surface of said tubular portion to support said outer radial surface.

16. The method as defined in claim 10, wherein said shape-memory material is also a radiopaque material.

17. The method as defined in claim 16, wherein said shape-memory material is formed of a nickel titanium alloy.

18. A method for attaching a marker to a medical instrument comprising the steps of:

providing a medical instrument having an outer surface and an inner chamber defined by an inner surface, at least one of said inner and outer surfaces being formed of a thermally responsive material which is softened at a softening temperature;

providing a marker formed of a shape-memory material capable of having a deformed configuration while at a first temperature and an original configuration at a second higher temperature;

lowering the temperature of said marker to said first temperature and deforming said marker;

positioning said marker in the deformed configuration adjacent to said inner or outer surface of thermally responsive material for subsequent engagement therewith; and raising the temperature or said shape-memory material to said second temperature and said softening temperature to soften said thermally responsive material while causing said shape-memory material to transform from said deformed configuration to said original configuration wherein said marker engages said medical instrument.

19. The method of claim 18 wherein said medical instrument includes a tubular portion of thermoplastic material wherein said outer surface is an outer radial surface of a first diameter and said inner surface is an inner radial surface of a second lesser diameter defining said inner chamber, said marker having a contact surface for contacting said tubular portion which, in the original configuration of said marker, is of a diameter which differs from the diameter of the inner or outer radial surface of the tubular portion to be engaged by said marker.

20. The method of claim 19 wherein said marker is a cylindrical band having an inner diameter in the original configuration which is less than the first diameter of the outer radial surface, and wherein the step of deforming said marker to said deformed configuration includes increasing the inner diameter of the cylindrical band to a diameter sufficient to permit the cylindrical band to fit over the outer radial surface of said tubular portion, the step of positioning said marker includes positioning said cylindrical band concentrically around the outer radial surface of said tubular portion, and the method further includes inserting a support into said inner chamber to support the inner radial surface.

21. The method of claim 19 wherein said marker is a cylindrical band having an outer diameter in the original configuration which is greater than the second diameter of the inner radial surface, and wherein the step of deforming said marker to the deformed configuration includes reducing the outer diameter of the cylindrical band to a diameter sufficient to permit the cylindrical band to be inserted within the inner chamber, the step of positioning said marker includes positioning said cylindrical band within the inner chamber adjacent to the inner radial surface thereof, and the method further includes positioning a support concentrically around the outer radial surface of said tubular portion to support said outer radial surface.

* * * * *